US009089620B2

(12) United States Patent
Henriot

(10) Patent No.: US 9,089,620 B2
(45) Date of Patent: Jul. 28, 2015

(54) AIR DECONTAMINATION DEVICE

(76) Inventor: Philippe Henriot, Francheville (FR)

(*) Notice: Subject to any disclaimer, the term of this patent is extended or adjusted under 35 U.S.C. 154(b) by 0 days.

(21) Appl. No.: 14/112,240

(22) PCT Filed: May 10, 2012

(86) PCT No.: PCT/FR2012/051037
§ 371 (c)(1),
(2), (4) Date: Oct. 17, 2013

(87) PCT Pub. No.: WO2012/153068
PCT Pub. Date: Nov. 15, 2012

(65) Prior Publication Data

US 2014/0056765 A1 Feb. 27, 2014

(30) Foreign Application Priority Data

May 11, 2011 (FR) ..................................... 11 54059

(51) Int. Cl.

| | |
|---|---|
| *A61L 2/00* | (2006.01) |
| *A61L 9/00* | (2006.01) |
| *A61L 9/03* | (2006.01) |
| *A61L 2/20* | (2006.01) |
| *A61L 9/015* | (2006.01) |
| *F24F 3/14* | (2006.01) |
| *F24F 3/16* | (2006.01) |

(52) U.S. Cl.
CPC . *A61L 9/03* (2013.01); *A61L 2/208* (2013.01); *A61L 9/015* (2013.01); *F24F 3/1405* (2013.01); *F24F 3/16* (2013.01); *A61L 2202/16* (2013.01); *A61L 2202/25* (2013.01); *A61L 2209/135* (2013.01); *A61L 2209/211* (2013.01); *F24F 2003/1675* (2013.01); *F24F 2221/125* (2013.01)

(58) Field of Classification Search
CPC ........... A61L 2/00; A61L 2/186; A61L 2/208; A61L 9/00; A61L 9/015; B01B 1/005
USPC ........... 422/1, 28, 31–32, 119, 123–125, 298, 422/305–307
See application file for complete search history.

(56) References Cited

U.S. PATENT DOCUMENTS

2005/0084415 A1 4/2005 McVey
2008/0135635 A1 6/2008 Deng

FOREIGN PATENT DOCUMENTS

EP 0 774 263 A1 * 5/1997 ................ A61L 2/20
EP 0774263 5/1997

(Continued)

*Primary Examiner* — Monzer R Chorbaji
(74) *Attorney, Agent, or Firm* — Mark M. Friedman

(57) ABSTRACT

The invention relates to an air decontamination device. The mobile air decontamination device (1) includes: (i) an inlet port and an outlet port; (ii) a dehumidifying means downstream from the inlet port for dehumidifying the air entering the device (1) via said inlet port; and (iii) a means for evaporating a microbicidal material, which is arranged upstream from the outlet port and downstream from the dehumidifying means, and which is intended for vaporizing the microbicidal material in the air flowing inside the device (1). Furthermore, the dehumidifying means includes a compressor (4) connected to the inlet port for compressing the air entering the device (1), a forced-convection condenser (5) arranged downstream from the compressor (4), and a water-separating filter (6) arranged downstream from the forced-convection condenser (5), the device (1) including a means for adjusting the discharge pressure of the compressor (4).

14 Claims, 3 Drawing Sheets

(56) References Cited

FOREIGN PATENT DOCUMENTS

Figure 1:
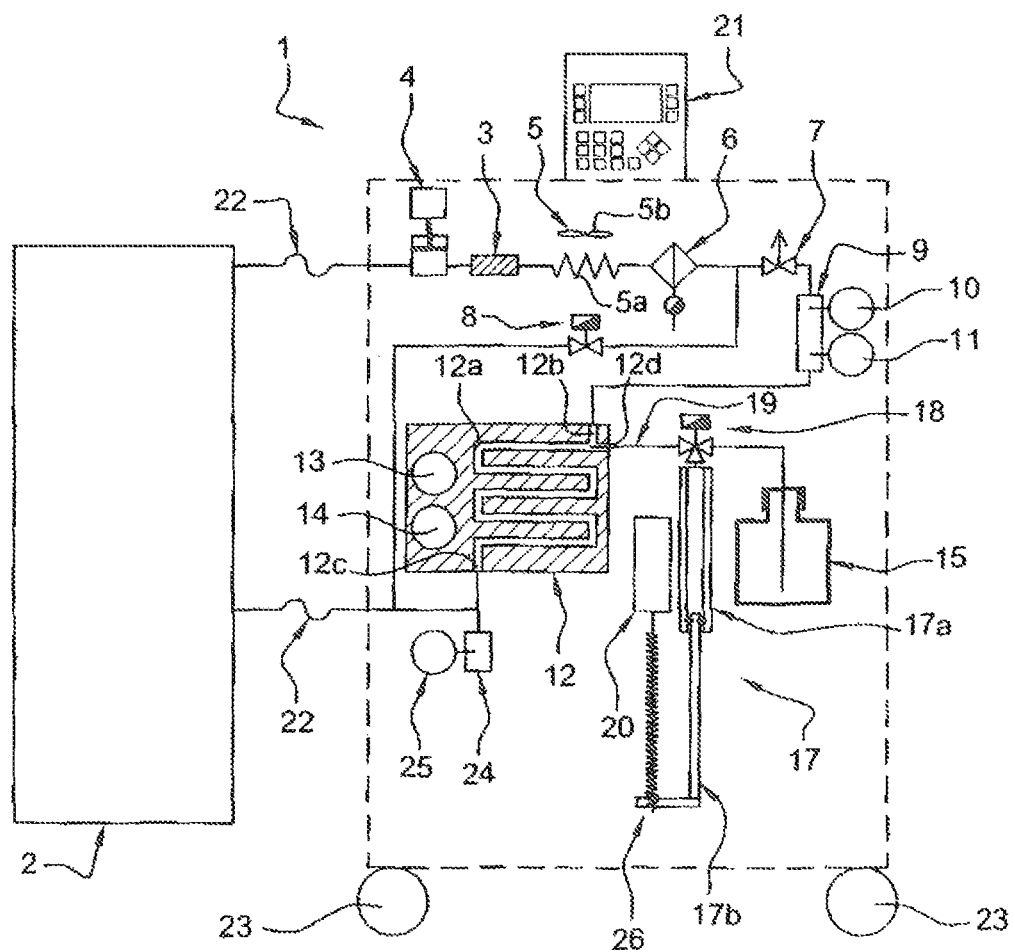

| WO | 2004020919 | 3/2004 |
| WO | 2007008205 | 1/2007 |
| WO | 2007102798 | 9/2007 |
| WO | 2008109252 | 9/2008 |

\* cited by examiner

AIR DECONTAMINATION DEVICE

The present invention relates to an air decontamination device.

The air decontamination device consists of diffusing a material having microbicidal properties into an atmosphere in order to substantially reduce the number of microbes living in that atmosphere. Air decontamination secondarily makes it possible to reduce the number of microbes present on the surfaces of the objects in contact with that atmosphere.

It is known to decontaminate premises using air decontamination devices diffusing a microbicidal material, for example glutaraldehyde, paracetic acid, or hydrogen peroxide. For the latter, increasingly valued for its advantages, there are two diffusion modes: atomization (diffusion of the material diluted at approximately 3% in the form of a mist) and vaporization (diffusion of the material concentrated at approximately 35% in gas form). The latter method is more effective due to the higher concentration, the great ease of diffusing the gas, the lack of material depositions under normal conditions, and other advantages. However, the concentrated material is highly corrosive, whereas the diluted material is not.

This gas diffusion may take place in an open circuit or closed-circuit. Compared to open-circuit diffusion, closed-circuit diffusion has the advantage of avoiding leaks of the microbicidal material outside the enclosure to be decontaminated (due to its toxicity for humans) or preventing it from being diluted by an outside air flow entering the enclosure to be decontaminated, which would decrease its effectiveness. Closed-circuit diffusion further offers the advantage of eliminating the need (due to the toxicity) to provide a discharge network outside the premises housing the enclosure, as is the case for open-circuit diffusion.

However, closed-circuit vaporization of a microbicidal material, such as a liquid containing hydrogen peroxide, leads to an increase in the relative humidity inside the enclosure. On the one hand, the liquid containing hydrogen peroxide diffused in the enclosure has a certain water content (for example 65%), and on the other hand, the conversion of the hydrogen peroxide leads to water formation. The increase in relative humidity may cause condensation of the vaporized hydrogen peroxide. The liquid deposits of hydrogen peroxide thus formed are very corrosive, whereas the gaseous form is much less so. This may cause the corrosion of the sensitive surfaces of the objects present in the enclosure on which the deposits have formed.

Furthermore, the existing decontamination devices are generally expensive to purchase and operate, sometimes require frequent maintenance operations, and may have a significant bulk or poor workability.

Known from patent document EP 0774263 is a sterilization apparatus using hydrogen peroxide vapor. However, the circulation of the air inside the apparatus described in patent document EP 0774263 is provided only by a fan that does not make it possible to deliver the air downstream at a pressure substantially higher than that of the upstream air. The humidity contained in the air circulating in the apparatus according to patent document EP 0177263 is therefore separated at atmospheric pressure. Furthermore, the separation is done by two refrigeration units operating alternating with each other and ensuring the separation by forming ice on their evaporators. This ice is then melted and extracted by a pump. The only compressors of the apparatus according to patent document EP 0774263 correspond to refrigeration compressors of the refrigeration units. They therefore do not have a compression effect on the air circulating in the apparatus according to patent document EP 0774263.

Known from patent document WO20081063252 is a modular decontamination system. The air circulating in the system is dried by passing through a column containing a hygroscopic gel. When the hygroscopic gel is saturated, it may be regenerated (dried) using a specific device. However, the system according to patent document WO2008/063252 has two drawbacks. On the one hand, the absorption capacity of the hygroscopic gel is limited, and once saturated, the column containing the hygroscopic gel will no longer make it possible to maintain low humidity in the enclosure to be decontaminated. On the other hand, in case of saturation of the hygroscopic gel, the column whereof the hygroscopic gel is saturated must be replaced by another column containing hygroscopic gel: this results in an additional time-consuming operation and requires having several hygroscopic gel columns on hand for replacement purposes.

Furthermore, the known devices traditionally comprise one or more peristaltic pumps to distribute the microbicidal material in the device for the evaporation thereof. The peristaltic pumps may be suitable for decontaminating enclosures with a relatively large volume. However, they do not allow satisfactory handling of small-volume enclosures (approximately several cubic meters). In fact, their flow rate can always be lowered to very low values, in the vicinity of several grams per hour. Consequently, to avoid overdosing microbicidal material in the enclosure to be decontaminated, the peristaltic pumps of the known devices are traditionally used intermittently: their operation consists of successive stops and starts. This results in irregular dosing of the microbicidal material in the enclosure to be decontaminated. Furthermore, the flow rate leaving a peristaltic pump is not very stable, has a pulsation, and is difficult to measure.

Consequently, the present invention aims to resolve all or part of the aforementioned drawbacks by proposing an air decontamination device by vaporizing a microbicidal material making it possible to control the relative humidity in a closed enclosure and having lower manufacturing, operating and maintenance costs.

To that end, the present invention relates to a mobile air decontamination device, comprising:
(i) an inlet port and an outlet port;
(ii) a dehumidifier means downstream from the inlet port for dehumidifying the air entering the device via said inlet port; and
(iii) a means for evaporating a microbicidal material, which is arranged upstream from the outlet port and downstream from the dehumidifier means, and which is intended for vaporizing the microbicidal material in the air flowing inside the device, characterized in that the dehumidifier means include a compressor connected to the inlet port, an ambient temperature cooler arranged downstream from the compressor, and a water-separating filter arranged downstream from the cooler. The compressor is intended to compress the air entering the device. It is suitable for compressing the air entering the device to a predetermined pressure P, to obtain the water saturation of the air having entered the device. The cooler advantageously corresponds to a forced-convection condenser and is suitable for cooling the air leaving the compressor and obtaining condensation at ambient temperature of the excess water contained in the air compressed by the compressor. The filter is suitable for collecting the condensed water owing to the forced-convection condenser. Lastly, the device also comprises adjusting means suitable for dropping the pressure of the air filtered by the filter to a pressure substantially below the predetermined pressure P, but sufficient to ensure the circulation in the device and in the enclosure to be decontaminated, as a fan could do.

Thus, it results from the laws of physics that by compressing the ambient air and containing the water in vapor form (humidity), then returning it to a temperature close to that which it had before the compression (the compression being accompanied by an increase in the temperature of the compressed air), that air becomes oversaturated and part of the water that it contains will then condense at ambient temperature (for example, approximately 20° C.). The device according to the invention thus offers the possibility of dehumidifying the air circulating inside the device and in the enclosure, without using a refrigeration machine or hygroscopic materials, as is the case in the traditional techniques.

According to another feature of the air decontamination device according to the invention, the evaporating means comprise an evaporator comprising a duct emerging on an upstream port and a downstream port, said evaporating means further comprising heating means of the evaporator, such as an electrical resistance, making it possible to heat the evaporator.

The heating means are suitable for increasing the temperature of the evaporator up to a predetermined temperature T. The predetermined temperature T is advantageously above the vaporization temperature of the microbicidal material.

According to one possibility, the evaporator corresponds to a metal block, the duct being machined in the metal block forming the evaporator.

According to one embodiment, the electrical resistance is inserted into a bore of the metal block forming the evaporator. According to one embodiment, the temperature probe monitoring the heating is inserted into a second bore of the metal block forming the evaporator.

Advantageously, the air decontamination device comprises means for injecting the microbicidal material inside a duct of the evaporating means. According to another feature of the air decontamination device according to the invention, the injection means comprise an injection needle having a first end emerging in the duct and a second end connected to a first path of a distribution valve, said distribution valve comprising a second path connected to a hollow body intended to contain the microbicidal material, said injection means further comprising a piston capable of sliding inside the hollow body and a screw-nut actuated by a motor to drive the translation of the piston in the hollow body. According to one possibility, the nut of said screw-nut system is secured to the piston.

This makes it possible to inject the microbicidal material inside the evaporator continuously so as to facilitate the evaporation thereof.

According to another feature of the air decontamination device according to the invention, the distribution valve comprises a third path intended to be connected to a reservoir.

Advantageously, the hollow body has a filling and expulsion port connected to the second half of the delivery valve, the filling and expulsion port being oriented upward.

In other words, the filling and expulsion port is arranged in the uppermost part of the hollow body.

The hollow body may be arranged substantially vertically.

In other words, the filling and expulsion port of the hollow body is the uppermost part of the hollow body. Thus, the air bubbles that may be suctioned with the microbicidal material during filling of the hollow body by the downward vertical travel of the piston do not drop to the bottom of the hollow body, but tend to remain in the upper part of the hollow body during filling thereof. A reverse travel of the piston makes it possible to discharge those air bubbles toward the reservoir, before modifying the position. The position of the delivery valve for that reverse travel of the piston makes it possible to expel the microbicidal material from hollow body toward the injection needle. This guarantees the absence of air in the microbicidal material when it is injected into the evaporator.

According to one embodiment, the device comprises means for indicating the position of the piston.

Advantageously, the means for indicating the position of the piston comprise a transducer.

The transducer may correspond to a linear taper potentiometer whereof the electrical resistance varies as a function of the movement of the piston.

Thus, the combination of the direction of movement of the piston and the orientation of the direction of the valve makes it possible to obtain the injection of the material in the evaporator, or the filling of the hollow body with microbicidal material from the reservoir. The combination of the direction of movement of the piston and the orientation of the delivery valve also makes it possible to empty the injection needle toward the hollow body and to empty the hollow body toward the reservoir.

According to another feature of the air decontamination device according the invention, the hollow body has, in the lower part, a port connected to a reversible pump and making it possible to fill the hollow body with microbicidal material from the reservoir, or to empty it toward the reservoir by reversing the direction.

According to one embodiment, the means for adjusting the pressure developed by the compressor are arranged downstream from the filter.

The means for adjusting the delivery pressure can advantageously comprise a valve.

The valve is advantageously arranged downstream from the forced-convection condenser and the filter. It is situated on the main air circulation circuit in the device connecting the input port and the output port.

The valve makes it possible to adjust the delivery pressure of the compressor.

According to one embodiment, the adjusting means are suitable for dropping the pressure of the air to a pressure close to atmospheric pressure.

Advantageously, the compressor has a constant flow rate.

Thus, it is not necessary to equip the device according to the invention with a regulating system and pressure sensors, which substantially reduces the cost thereof.

According to one embodiment, the predetermined pressure P is greater than or equal to 3 bars, for example greater than or equal to 4 bars or greater than or equal to 5 bars.

According to another feature of the air decontamination device according to the invention, said device comprises a bypass valve.

The bypass valve is advantageously arranged on the secondary circuit, extending from downstream of the filter to the outlet port of the device.

Preferably, the air decontamination device according to the invention comprises an air heater placed downstream from the water-separating filter and upstream from the evaporator, said air heater making it possible to increase the temperature of the air leaving the water separator filter.

This feature offers the advantage of making it possible to inject a greater quantity of microbicidal material into the air circulating in the device than if that air was not heated.

According to one embodiment, the device comprises an air heater arranged in the duct, upstream from the injection point where the injection needle emerges, so as to increase the temperature of the air before the injection of microbicidal material.

Advantageously, the air decontamination device according to the invention comprises a bent reservoir connected to the downstream port on the one hand and the outlet port on the other hand.

This feature makes it possible to collect the droplets leaving the evaporator that would form in the case of a malfunction of the system, thus preventing non-evaporated, and therefore highly corrosive, liquid microbicidal material from being sent into the enclosure.

According to another feature of the air decontamination device according to the invention, the cooler or forced-convection condenser comprises a metal tube and a fan making it possible to hold the metal tube by propelling ambient air toward said metal tube.

Advantageously, the device comprises additional cooling means intended to cool the air leaving the compressor as a supplement to the forced-convection condenser.

For example, the additional cooling means comprise a Peltier effect module.

According to still another feature of the air decontamination device according to the invention, the cooler comprises a refrigerating machine.

This feature offers the possibility of lowering the temperature of the air significantly, to temperatures below the ambient air temperature, for example a temperature lower than or equal to 5° C.

Advantageously, the air decontamination device according to the invention comprises casters.

Preferably, the air decontamination device according to the invention comprises two hoses for connecting to the enclosure.

This feature offers the advantage of making it possible to use the device according to the invention outside the enclosure, which makes it possible to operate on the device without entering the enclosure whereof the air contains the microbicidal material.

Advantageously, the microbicidal material is a liquid containing hydrogen peroxide and water.

According to still another feature of the air decontamination device according to the invention, said device comprises a catalyst placed downstream from the compressor.

The invention will be better understood using the following detailed description of one embodiment of the invention, described below in light of the appended drawings, in which:

FIG. 1 shows a cross-sectional diagrammatic profile view of an air decontamination device according to one particular embodiment of the invention, FIG. 2 shows a diagrammatic cross-sectional profile view of an air decontamination device according to another specific embodiment of the invention, FIG. 3 is a diagrammatic cross-sectional profile view of an air decontamination device according to another embodiment of the invention.

FIG. 1 diagrammatically shows an air decontamination device 1 according to one particular embodiment of the present invention. The air decontamination device 1 is suitable for decontaminating the air contained in a closed enclosure 2 by vaporizing a microbicidal material such as a liquid containing hydrogen peroxide. Secondarily, the air decontamination device 1 makes it possible to decontaminate the surface of the objects present inside the enclosure 2. The decontamination cycle may include a decontamination phase strictly speaking, during which the microbicidal material is vaporized and injected into the enclosure 2, followed by a phase for gradually decreasing the hydrogen peroxide content contained in the air of the enclosure 2.

The device 1 comprises an inlet port and an outlet port respectively allowing the intake of the air contained in the enclosure 2 inside the device 1 and the expulsion of that air outside the device 1, toward the inside of the enclosure 2.

As shown in FIGS. 1 and 3, the device 1 comprises means for dehumidifying the air. These dehumidifying means are in particular formed by a compressor 4, a cooler and a filter 6.

The cooler advantageously corresponds to a forced-convection condenser 5, as illustrated in FIGS. 1 and 3.

The compressor 4 ensures the circulation of the air inside the device 1, and therefore the enclosure 2, due to the closed-circuit system. It suctions the upstream air, which it delivers downstream, toward a catalyst 3 installed as output and toward the cooler. Upstream and downstream are defined relative to the circulation direction of the air inside the device 1. The air leaving the compressor 4 and next entering the catalyst 3 has a higher pressure and temperature than upstream, due to the compression. This high temperature advantageously accelerates the dismutation of the hydrogen peroxide in the catalyst 3, making it possible to break it down into water and dioxygen. In one alternative embodiment, the catalyst 3 may also be connected to the inlet port of the device 1, i.e., it may be placed upstream from the compressor 4 instead of being placed downstream, as shown in FIG. 2.

The outlet pressure of the compressor 4 is advantageously greater than 3 bars, 4 bars or 5 bars.

The compressor 4 is arranged on the trajectory of the air entering the device 1: the air entering the device 1 necessarily goes to the compressor 4. The compressor 4 is in fact placed on the main air circulation circuit in the device 1.

The compressor 4 is advantageously a constant flow positive displacement compressor. There is therefore no need to provide flow measuring sensors and a system for regulating the airflow circulating in the device 1, which helps reduce costs.

During the decontamination phase, the use of the catalyst 3 may make it possible, over the course of the decontamination cycle, to monitor the content level of hydrogen peroxide in the air. At the end of the decontamination phase, the use of the catalyst 3 makes it possible to gradually decrease the hydrogen peroxide content level of the air circulating in the device 1, and consequently that of the air of the enclosure 2.

The cooler or forced-convection condenser 5 may include a metal tube 5*a*, for example made from aluminum or stainless steel, so as to withstand corrosion due to the residual hydrogen peroxide that may remain at the outlet of the catalyst 3. The cooler or forced-convection condenser may further include a fan 5*b* allowing cooling of the metal tube 5*a* with the ambient air.

The forced-convection condenser 5 is arranged so that the air at the outlet of the compressor 4 circulates in the metal tube 5*a*.

The fan 5*b* is arranged to generate a flow of ambient air toward the metal tube 5*a*.

The cooler may also comprise a refrigerating machine, for example an absorbing machine, making it possible to decrease the temperature of the compressed air to values less than or equal to 5° C.

According to one embodiment, the device 1 may comprise a Peltier effect module 27 as a supplement to the forced-convection condenser 5.

As shown in FIG. 3, the Peltier effect module 27 is arranged downstream from the forced-convection condenser 5, and upstream from the water-separating filter 6. The Peltier effect module 27 makes it possible to still further decrease the quantity of water contained in the compressed air, by cooling it more, for example to a temperature close to 0° C.

Under the effect of the cooling, the compressed air become saturated with water. The excess water that it initially contained but that it henceforth can no longer contain in gaseous form then condenses; water droplets form.

These droplets are filtered using the water-separating filter 6. The water-separating filter 6 is placed downstream from the cooler or forced-convection condenser 5, and if applicable Peltier effect module 27. The filter 6 may make it possible to filter droplets with a diameter of approximately several microns. An automatic bleed of the filter 6 may be provided to make it possible to discharge the water amassed by the filter 6. At the outlet of the filter 6, the air is expanded. Its volume increases. The quantity of water that it contained has been reduced. Its relative humidity is thus decreased.

It will be noted that the water-separating filter 6 with automatic bleed is installed downstream from the forced-convection condenser 5 and allows the automatic discharge of the water without having to use an extraction pump.

As an example, the air of the enclosure 2, whereof the temperature is 20° C. and the relative humidity is 60%, contains 9 g of water per kilogram of air. Suctioned and compressed at 5 bars by the compressor 4, the temperature of this suctioned and compressed air will rise to a value of approximately 150° C. This increased temperature accelerates the dismutation of the hydrogen peroxide in the catalyst 3. This compressed air, then cooled to a temperature of approximately 20° C. by the cooler or forced-convection condenser 5, is oversaturated and then cannot contain more than 2.7 g of water per kilogram of air instead of 9 g of water per kilogram of air (see table below). Its relative humidity is then 100%. The filter 6 makes it possible to eliminate the excess water, condensed in the form of droplets. The air at the outlet of the filter 6, containing 2.7 g of water per kilogram of air, is then expanded; its volume increases. Its relative humidity will be 17%, whereas it was initially 60%.

To obtain the same hygrometry of 17% without compression, it would be necessary to cool it to −5° C. instead of 20° C., in other words to convert the water it contains into ice. The device 1 according to the invention makes it possible to eliminate that need.

If a Peltier effect module 27 is installed and returns the temperature of the compressed air to a temperature of approximately 0° C., the latter then cannot contain more than 0.6 g of water per kilogram of air instead of 9 g of water per kilogram of air. Its relative humidity (by bringing the temperature to 20° C.) is then 4%, whereas it was initially 60%. To obtain the same hygrometry of 4% without compression, it will be necessary to cool it to approximately −25° C. instead of 0° C. It is also possible to consider using a hygroscopic gel.

The following comparative table shows the difference in results obtained in terms of quantity of residual water contained in the air when the latter is cooled to a temperature T without having been compressed beforehand (case of a device whereof the circulation of the air is ensured by a fan only), and when the latter is cooled after having been compressed to five bars (as is the case with the device 1, owing to the compressor 4):

|  | T | | |
| --- | --- | --- | --- |
|  | 20° C. | 10° C. | 0° C. |
| Air cooled without compressing it | 9 g/kg | 7.5 g/kg | 3.8 g/kg |
| Air cooled after compression at 5 b | 2.7 g/kg | 1.2 g/kg | 0.6 g/kg |

The above table clearly shows that the dehumidification of the air circulating in the device 1 is substantially greater (lower quantity of residual water) when the air has been compressed by the compressor 4 before being cooled. It is therefore possible to see the interest of compressing the air entering device 1 to effectively dehumidify that air.

Figure 2:
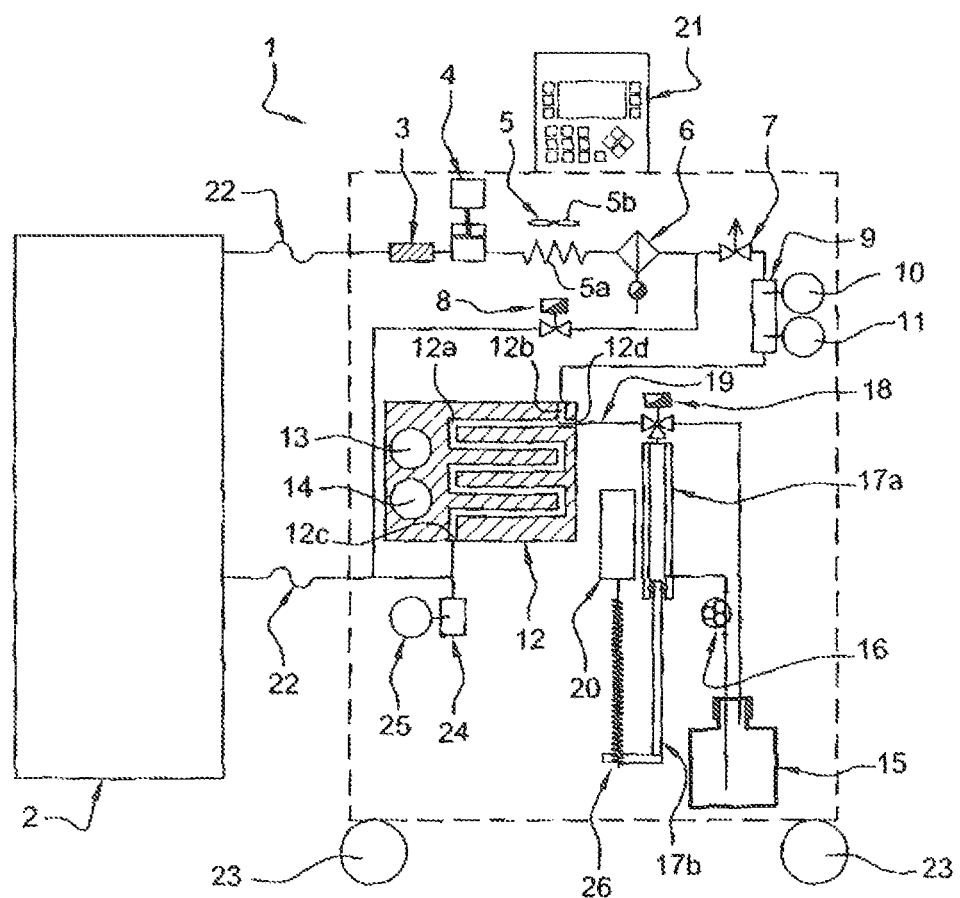
Figure 3:
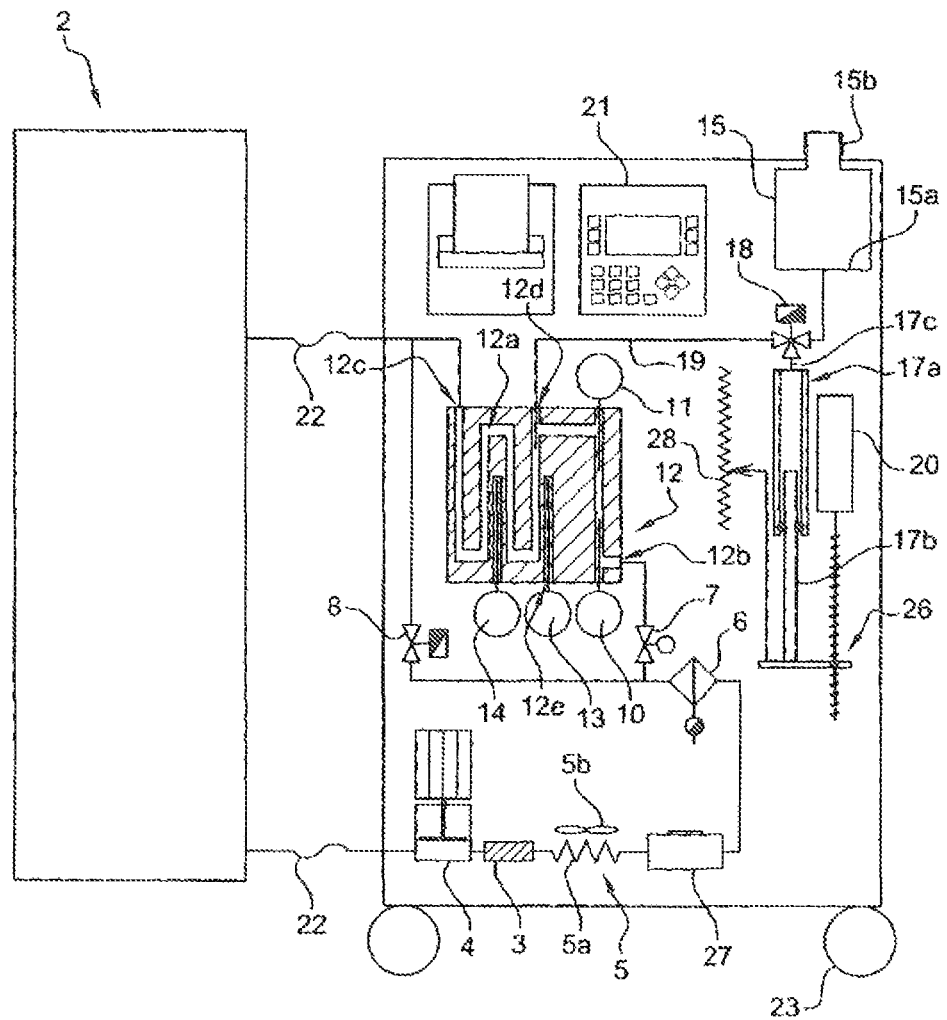

As shown in FIGS. 1 to 3, it is possible to provide means for adjusting the delivery pressure of the compressor 4, such as a needle valve 7 downstream from the filter 6. This allows a user of the device 1 to select the residual humidity level of the air at the outlet of the filter 6.

The valve 7 is advantageously placed downstream from the filter 6, to expand the air that has been previously compressed, cooled and filtered. It will be noted that the pressure at the outlet of the valve 7 may be close to the atmospheric pressure, but sufficient to ensure circulation in the device and in the enclosure to be decontaminated.

It is also possible to provide an automatic bypass valve 8, also placed downstream from the filter 6, in parallel with the needle valve 7. The bypass valve 8 is intended to open at the end of the decontamination phase so as to make it possible to decrease the pressure at the outlet of the compressor 4. The airflow rate suctioned, then delivered by the compressor 4 is thus increased. This makes it possible to accelerate the circulation of the air inside the device 1, in particular in the catalyst 3. The hydrogen peroxide content level inside the air contained in the enclosure 2 is thus rapidly reduced.

As shown in FIGS. 1 to 3, the bypass valve 8 is arranged on a secondary (bypass) circuit extending from downstream of the filter 6 to the outlet port of the device 1.

Downstream from the valve 7, it is possible to provide an air heater 9 for example comprising an electrical resistance 10 and a temperature probe 11 making it possible to monitor the temperature of the air heater 9. This air heater 9 makes it possible to heat the dehumidified air so as to increase the quantity of hydrogen peroxide that will be able to be injected into that air without it being saturated.

The device 1 may comprise a reservoir 15 or be intended to be connected to such a reservoir making it possible to store the microbicidal material. The microbicidal material is advantageously a liquid containing 35% hydrogen peroxide and 65% water.

The device 1 comprises evaporating means for the microbicidal material, for example formed by an evaporator 12. The evaporator 12 is a metal part, for example made from aluminum or stainless steel. It comprises a duct 12a provided with an upstream inlet port 12b and a downstream outlet port 12c. Advantageously, the duct 12a has a diameter calculated to obtain a high airspeed, and also has one or more baffles. In the described embodiment, the evaporator 12 comprises an electrical resistance 13 intended to be heated to a temperature above the boiling temperature of the microbicidal material, such that any deposition thereof evaporates immediately. It also comprises a temperature probe 14 making it possible to monitor that temperature. For a liquid containing 35% hydrogen peroxide and 65% water, the temperature of the evaporator 12 may for example be 110° C.

The evaporator 12 advantageously assumes the form of a metal block in which the duct 12a is machined.

The electrical resistance 13 may assume the form of a cylindrical cartridge inserted into a bore 12e of the metal block forming the evaporator 12. The temperature probe 14 may also be inserted into that bore 12e (or into a separate bore) in order to regulate temperature of the electrical resistance 13.

The device 1 also comprises means for injecting microbicidal material inside the evaporator 12. These injection means comprise an injection needle 19, a distribution valve 18, a longitudinal hollow body 17a in which a piston 17b is intended to slide, a motor 20, and a screw-nut system 26. The hollow body 17a may have a cylindrical cavity, and the piston 17b may also be cylindrical.

The motor 20 may operate in both directions of rotation, to move the piston 17b in one direction or the other, and can also operate at a variable speed.

The injection needle 19, whereof the inner passage of the material is very reduced so as to have a significant speed even with a very low material flow rate, has a first end emerging in the duct 12a and a second end connected to the distribution valve 18.

The first end of the injection needle 19 emerges in the duct 12a at the injection point 12d.

The baffles of the duct 12 favor the deposition of still-liquid material and favor its evaporation. The high speed of the air, created by the flow rate of the compressor 4 and the diameter of the duct 12a, will facilitate the removal of the microbicidal material once it leaves the injection needle 19.

According to FIG. 3, in its upstream part at the injection point 12d, the machined duct 12a may comprise the air heater 9. The latter may assume the form of a cartridge inserted into the axis of the duct 12a with a sealing system. The air heater 9 makes it possible to heat the air previously dehumidified so as to increase the quantity of microbicidal material that will be able to be injected into that air without saturating it.

Thus, in its upstream part at the injection point 12d, the machined duct 12a may comprise the electrical resistance 10 and the temperature probe 11. The upstream part at the injection point 12d of the duct 12a may therefore be configured to receive the electrical resistance 10 and, if applicable, the temperature probe 11. It may be substantially rectilinear. Thus, in its upstream part at the injection point 12d, the machined duct 12a may comprise the air heater 9 in the form of a cartridge inserted into the axis of the duct 12a.

As an example, for a compressor 4 delivering 2 $m^3$/hour of air, the diameter of the duct 12a of the evaporator 12 may be 5 mm, which is an airspeed of 30 m/s. The flow rate of microbicidal material leaving the injection needle 19 necessary for the decontamination method may then be adjusted to 40 ml (0.04 liters/hour), which is very low, but the passage speed of the microbicidal material in the injection needle 19 (the inner diameter of which is 0.13 mm) will be 0.8 m/s. The microbicidal material thus leaves the injection needle 19 continuously and not drop by drop.

The microbicidal material reaches the end of the injection needle 19 emerging in the duct 12a. This material is removed by the hot air flow circulating in the duct 12a, such that it vaporizes at least partially by drying. The residual droplets are projected on the walls of the duct 12a, which is favored by the high circulation speed of the air and the existence of the baffles. They then vaporize in contact with the latter.

The piston 17b is able to slide inside the hollow body 17a. The sealing between the piston 17b and the hollow body 17a may be provided by an O-ring. The piston 17a is connected to the nut of the screw-nut system 26. The screw of the screw-nut system is in turn rotated by a motor 20. Thus, the motor 20 rotates the screw, which in turn causes translation of the piston 17b in the hollow body 17a. The motor 20 may be electric, variable speed, its speed and direction of rotation being controlled by an instruction.

The distribution valve 18 also communicates with the reservoir 15. The hollow body 17a has, at its uppermost point, a port connected to one of the three paths of the distribution valve 18.

According to one embodiment, the reservoir 15 is advantageously positioned above the distribution valve 18 so as to facilitate the gravitational flow of the microbicidal material toward the distribution valve 18 and the hollow body 17a.

As illustrated in FIG. 3, the bottom 15a of the reservoir 15 is connected to the distribution of valve 18.

It will further be noted that the neck 15b of the reservoir 15 emerges outside the device 1 to facilitate the introduction of microbicidal material into the reservoir 15.

During filling of the hollow body 17a, the distribution valve 18 orients the microbicidal material from the reservoir 15 toward the inside of the hollow body 17a, the transfer of the liquid containing hydrogen peroxide being ensured by a translational movement of the piston reversed relative to that ensuring the injection.

Before injecting the material, the movement of the piston 17b may be provisionally reversed without reversing the position of the valve 18 so as to discharge, toward the reservoir, the air bubbles that may be present, and which will remain in the upper part during and after filling. Thus, the microbicidal material then injected into the evaporator 12 is free of air bubbles.

During the injection of the microbicidal material inside the evaporator 12, the distribution valve 18 orients that material toward the injection needle 19. The microbicidal material is then gradually expelled outside the hollow body 17a owing to the translation of the piston 17b.

At the end of the cycle, it is possible to empty the entire circuit by orienting the expulsion of the microbicidal material toward the reservoir 15 by inverting the distribution valve 18, so as to prevent stagnation of the material between two cycles, and so as to facilitate any maintenance operations. It will also be possible to empty the injection needle 19 toward the inside of the hollow body 17a by simultaneously reversing the direction of translation of the piston 17b and the orientation of the distribution valve 18.

The direction of movement of the piston 17b and the orientation of the distribution of the valve 18 make it possible to obtain, according to the following combinations: the injection of the microbicidal material in the evaporator 12, the filling of the hollow body 17a of the cylinder 17 with microbicidal material from the reservoir 15, the emptying of the injection needle 19 toward the hollow body 17a of the cylinder 17, and the emptying of the cylinder 17 and the reservoir 15.

According to one alternative embodiment, shown in FIG. 2, the hollow body 17a may also comprise, in the lower part, a port connected to a reversible pump 16, which in turn is connected to the reservoir 15. The third path of the valve 18 is then connected to the upper part of the reservoir 15. This device makes it possible to fill the hollow body with microbicidal material from the reservoir, or to empty it toward the reservoir by reversing the direction.

The injection means advantageously make it possible to obtain a very low flow rate of microbicidal material in the evaporator 12, such that the flow rate is constant, including to treat enclosures with a small volume. For example, for an enclosure to be decontaminated corresponding to a service hatch with a volume of 0.125 $m^3$ (cubic volume whereof the edge is for example 50 cm) in which one wishes to obtain a concentration of 500 ppm in microbicidal material with an air flow rate circulating in the device of 2 $m^3$/h (by means of the compressor 4), the flow rate of microbicidal material injected into the evaporator 12 must be approximately 4 g/h. The traditional devices generally equipped with peristaltic pumps do not make it possible to achieve such a low flow rate.

A control and command system 21 is provided to manage the operation of the device 1 during the successive cycles for decontamination and decreasing the hydrogen peroxide content level.

According to one possibility illustrated in FIG. 3, the device 1 comprises means for indicating the position of the piston 17b to deduce therefrom, at any moment, the volume, therefore the quantity of microbicidal material injected into the evaporator 12. The means for indicating the position of the piston 17b may in particular comprise a transducer 28. The transducer 28 then advantageously makes it possible to convert a property representative of the position of the piston 17b, for example into an electrical signal proportional to the distance between the position of the piston 17b at a moment t and one of the two extreme positions it may adopt. The transducer 28 may correspond to a linear taper potentiometer, the electrical resistance of which may be proportional to the distance in question.

The device 1 may further include connecting means, for example hoses 22. A first end of one of the hoses 22 is connected to the input (or output) port of the device 1. A second end of the cells 22 emerges inside the enclosure 2.

On the flexible link bringing air from the enclosure 2 toward the device 1, it is possible to install a device for measuring the hydrogen peroxide content level extracted from the enclosure 2 so as to verify that the cycle progressed correctly and that the content level of hydrogen peroxide in the air was reduced to an acceptable value, i.e., a value for which there is no risk for a person entering the enclosure 2, at the end of the decontamination cycle.

The device 1 may also be equipped with rolling means, for example casters 23.

The device 1 may include a bent reservoir 24, placed at the outlet of the evaporator 12. The bent reservoir 24 makes it possible to collect the droplets that would form in case of a malfunction of the system, thereby preventing non-evaporated, and therefore highly corrosive, liquid microbicidal material from being sent into the enclosure. A level probe 25 may be attached to the bent reservoir 24 to alert a user to the existence of such a malfunction.

Although the invention has been described relative to specific example embodiments, it is of course in no way limited thereto and encompasses all technical equivalents of the described means as well as combinations thereof if they are within the scope of the invention.

The invention claimed is:

1. A mobile air decontamination device, comprising:
   (i) an inlet port and an outlet port;
   (ii) a dehumidifier downstream from the inlet port for dehumidifying the air entering the device via the inlet port, the dehumidifier including a displacement compressor in communication with the inlet port and configured for compressing the air entering the device up to a predetermined pressure and for ensuring the circulation of the air inside the device, a forced-convection condenser downstream from the displacement compressor to cool the air leaving the displacement compressor and obtain condensation at ambient temperature of the excess water contained in the air compressed beforehand, a water-separating filter positioned downstream from the force-convection condenser to collect the condensed water;
   (iii) a pressure adjustment mechanism configure for adjusting the pressure of the air filtered by the filter to drop to a pressure substantially below the predetermined pressure; and
   (iv) an evaporation mechanism for evaporating a microbicidal material, the evaporation mechanism arranged upstream from the outlet port and downstream from the dehumidifier, the evaporation mechanism configured for vaporizing the microbicidal material in the air flowing inside the device.

2. The air decontamination device of claim 1, further comprising:
   (i) an injection for injecting the microbicidal material inside a duct of the evaporation mechanism the injector comprising an injection needle having a first end emerging in the duct and a second end communicating with a hollow body configured for containing the microbicidal material, the injector further comprising a piston capable of sliding inside the hollow body and a screw-nut system actuated by a motor to drive the translation of the piston in the hollow body.

3. The air decontamination device of claim 2, further comprising:
   (i) a distribution valve including three paths, a first path of the distribution valve in communication with the second end of the injection needle, a second path of the distribution valve in communication with an expulsion port located at the uppermost point of the hollow body, and a third path of the distribution valve in communication with a reservoir.

4. The air decontamination device of claim 2, further comprising:
   (i) a position indicator for indicating the position of the piston.

5. The air decontamination device of claim 2, wherein the hollow body has, at the lowest point, a filling and emptying port in communication with a reversible pump making it possible to fill or empty the hollow body with microbicidal material from a reservoir.

6. The air decontamination device of claim 2, further comprising:
   (i) an air heater arranged in the duct, upstream from an injection point where the injection needle emerges, in order to increase the temperature of the air before the injection of microbicidal material.

7. The air decontamination device of claim 1, wherein the evaporation mechanism comprises an evaporator comprising the duct emerging on an upstream port and a downstream port, the evaporation mechanism further comprising a heating member for heating the evaporator, the evaporator corresponding to a metal block and the duct being machined in the metal block forming the evaporator.

8. The air decontamination device of claim 7, wherein the heating member comprises an electrical resistance inserted into a bore of the metal block forming the evaporator.

9. The air decontamination device of claim 1, wherein the pressure adjustment mechanism includes a valve.

10. The air decontamination device of claim 1, wherein the predetermined pressure is greater than or equal to 3 bars.

11. The air decontamination device of claim 1, wherein the forced-convection condenser comprises a metal tube and a fan making it possible to cool the metal tube by propelling the ambient air toward the metal tube.

12. The air decontamination device of claim 1, further comprising:
    (i) a complementary cooling mechanism configured for cooling the air leaving the displacement compressor in addition to the forced-convection condenser.

13. The air decontamination device of claim 1, further comprising:
    (i) a bypass valve.

14. The air decontamination device of claim 1, wherein the device includes a catalyst placed upstream from the displacement compressor.

* * * * *